(12) United States Patent
Batiste et al.

(10) Patent No.: US 8,978,178 B2
(45) Date of Patent: Mar. 17, 2015

(54) ANTI-WRINKLE FABRIC ARRANGEMENT

(76) Inventors: Stan Batiste, Granite Bay, CA (US); Maryann Batiste, Granite Bay, CA (US); Steven Achstein, Roseville, CA (US)

( * ) Notice: Subject to any disclaimer, the term of this patent is extended or adjusted under 35 U.S.C. 154(b) by 194 days.

(21) Appl. No.: 13/372,378

(22) Filed: Feb. 13, 2012

(65) Prior Publication Data

US 2012/0227185 A1 Sep. 13, 2012

Related U.S. Application Data

(60) Provisional application No. 61/463,084, filed on Feb. 11, 2011.

(51) Int. Cl.
*A47G 9/02* (2006.01)
*A47G 9/00* (2006.01)

(52) U.S. Cl.
CPC .............. *A47G 9/0253* (2013.01); *A47G 9/007* (2013.01); *Y10S 5/926* (2013.01)
USPC ................ 5/490; 5/482; 5/502; 5/636; 5/926; 5/421

(58) Field of Classification Search
USPC ............. 5/641, 490, 421, 495, 482, 485, 640, 5/727, 737, 740, 655.9, 925, 926, 953, 5/486, 497, 499, 722; 442/182, 246, 255, 442/327; 2/69
See application file for complete search history.

(56) References Cited

U.S. PATENT DOCUMENTS

| | | | | |
|---|---|---|---|---|
| 6,145,143 | A * | 11/2000 | Hicks et al. | 5/722 |
| 6,421,859 | B1 * | 7/2002 | Hicks et al. | 5/722 |
| 6,516,483 | B1 * | 2/2003 | VanSteenburg | 5/737 |
| 2008/0264512 | A1 | 10/2008 | Metzger | |
| 2011/0167532 | A1 | 7/2011 | Carlson et al. | |

* cited by examiner

*Primary Examiner* — Peter M Cuomo
*Assistant Examiner* — Brittany Wilson
(74) *Attorney, Agent, or Firm* — Weide & Miller, Ltd.

(57) ABSTRACT

The present invention relates to a fabric arrangement and pillow designed to prevent skin lines and wrinkle formation while improving sleep using combinations of fabrics, cooling technologies and scents. The present invention is designed with a specific fabric and materials combination that create a surface in which the shear stresses causing skin lines and wrinkles are eliminated. Multiple layers make up the fabric arrangement include a top layer comprising a stretchable material and a second layer comprising a low friction material relative to the first layer. Supporting the first two layer is a support layer such as foam. Lower layers may comprise a cooling material, an antimicrobial or anti-allergenic material and a scent layer.

15 Claims, 5 Drawing Sheets

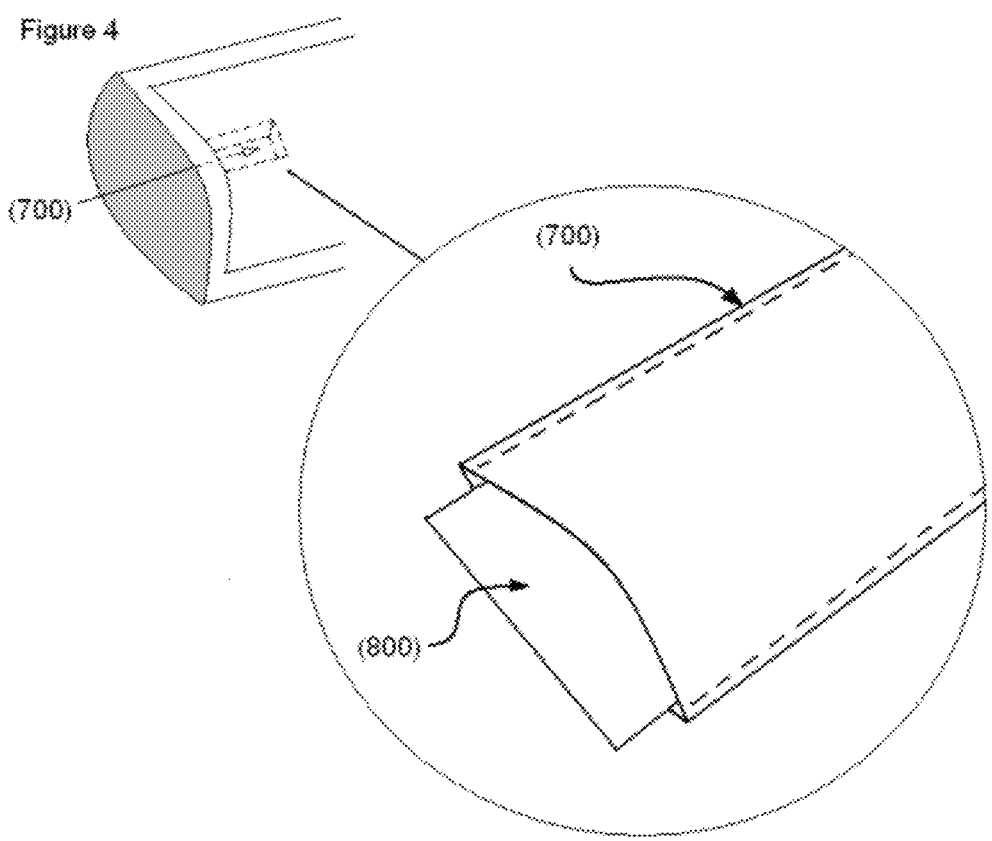

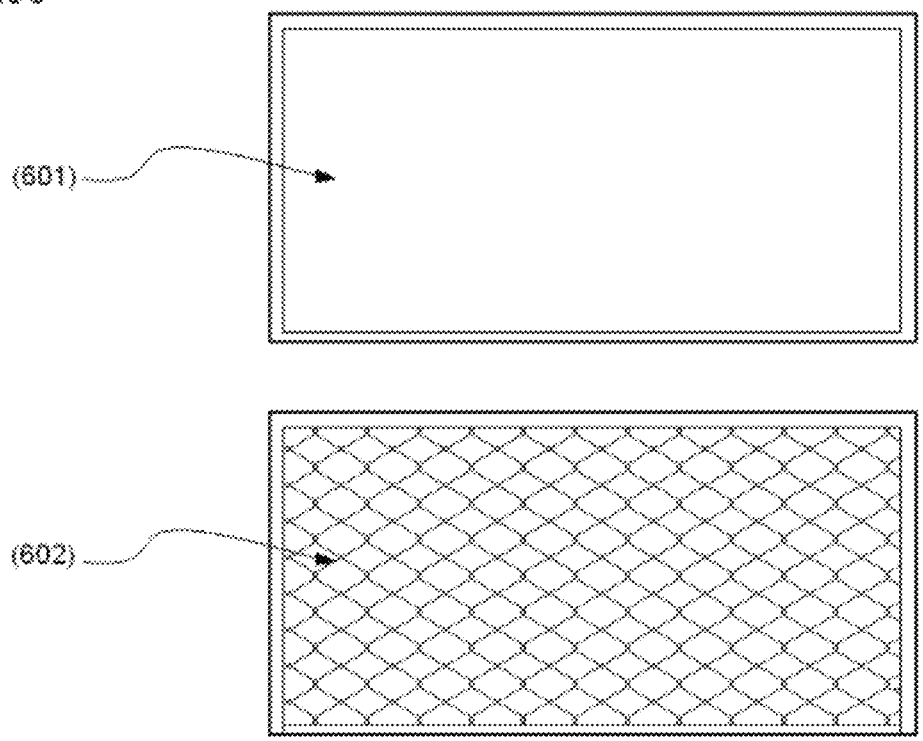

ANTI-WRINKLE FABRIC ARRANGEMENT

1. PRIORITY CLAIM

This application claims priority to and the benefit of U.S. Provisional Patent Application No. 61/463,084 filed on Feb. 11, 2011 titled Anti-Wrinkle Spa Pillow.

2. FIELD OF INVENTION

The present invention relates to fabric arrangement and in particular to a method and apparatus for reducing wrinkles and skin tension.

3. DESCRIPTION OF RELATED ART

Wrinkles are typically associated with old age and an unyouthful appearance. As a result, people often try to reduce the appearance of skin wrinkles and often take steps to reduce the creation of wrinkles.

Numerous different approaches have been proposed in the past to reduce or eliminate wrinkles. This approach typically focuses on the face and neck and may take the form of a pillow, which supports the face and neck during sleep. The approaches may be classified into physical, medical, or chemical in nature. One prior art approach is in the form of a contour type pillow which is designed to keep the skin off the surface of the pillow. This approach suffers from the inherent difficulty in attempting to keep a user's skin off the pillow and the discomfort that causes the user, which may interrupt normal sleep patterns.

Another approach is set forth in U.S. Pat. No. 5,084,928 titled Pillowcase Formed of Elastic Fabric. This prior art approach simply provides an elastic pillowcase into which the pillow is compressed. This pillow compressed inside the pillowcase in combination with the elastic pillowcase is proposed to be made so taut that it will not wrinkle, and hence will not transfer wrinkles to the user of the pillow. This approach suffers from the drawback of changing the hardness and density of the pillow itself, which causes the pillow to become significantly more firm. Hence, the pillow may provide too much support to the user. In addition, the pillow still wrinkles when the weight of the user's head compresses the pillow and elastic material.

A third approach prevent wrinkles involves use of cloth fabric as the pillow covering with a high number of threads per inch. The asserted benefit to using a high thread count fabric is that such fabric decreases the loss of moisture and provides a smooth surface for the skin. Finally, chemical based approaches include designs which use copper imbedded into the material of the pillow. The copper is asserted to help prevent wrinkles by reducing bacterial buildup in the pillow due to the copper's ability to reduce bacteria. The reduced bacterial level is asserted to reduce damage to the skin and thereby also reduce wrinkles. However, Both of these proposed wrinkle reduction method suffer from drawbacks. The use of high thread count sheets create more expensive and delicate product, while the use of copper is not only expensive, but can be washed away during laundering.

The innovation described below, overcomes the drawbacks associated with the prior art and provides additional benefits.

SUMMARY

Disclosed herein is a pillow with specific features that prevent skin lines and wrinkle formation while improving sleep using combinations of fabrics, cooling technologies and scents. The disclosed fabric arrangement allows the user to sleep in a normal fashion using what feels like their normal pillow instead of other anti-wrinkle pillow designs which generally use various shapes to keep the skin away from the pillow surface.

As we age, the appearance of sleep wrinkles, those facial lines that develop from sleeping with your face against a pillow, becomes much more prominent. This should come as no surprise if you consider how much of one's life is spent sleeping. If you are getting the recommended 8 hours of sleep per night, you sleep ⅓ of your life. Consequently, by age 60, you will have slept 20 years. It is obvious why sleeping on our face eventually leads to creases that become permanently etched in the surface of the skin. When the skin becomes creased while sleeping, it no longer able to readily snap back when the head is not resting on the pillow, as it did when we were younger. Sleep wrinkles are much easier to prevent than they are to repair.

The sleep lines referred to herein are initially temporary creases in the skin that when a person is young disappear after a few minutes to within hours of waking up. Sleep lines are a result of shear stresses and direct forces acting on the skin from long term contact from a pillow. When young, the skin has the elasticity that can withstand these pressures. As people age their skin becomes less resilient and these lines become permanent wrinkles, continually increasing in number, length and depth.

According to the numerous dermatologists, wrinkles are a result of both internal forces created from physiologic changes in the skin and external forces such as pressure on the skin surface and environmental factors such as the sun. The three major forces that are responsible for sleep lines are shear stress, direct pressure and pressures exerted on the bunching of materials and their related forces.

Sleep lines caused by shear stress are a result of parallel differential motion of your skin relative to the pillow. As a person moves, their skin moves over the pillow fabric surface and as a result, friction and associated shear stress is created. The shear stress stops a region of the skin from moving and it then bunches up and forms creases.

The sleep line has a second component which is the force created by the weight of the head acting in a perpendicular direction to the shear stress. This force then acts upon the sleep line by increasing the pressures further deforming the skin.

The final factor causing the creation of sleep lines is that of material bunching and pressure. When you look at most pillows there are fabric wrinkles that naturally occur due to excess materials. As a person sleeps they move and this creates waves of material that can "bunch-up" under their skin. This bunched-up material with the exerted pressures of your head result in sleep lines.

Stretchable Layer and Sheer Stress

Systems and method for counteracting the forces of sheer and direct pressure, while keeping the experience of sleeping on a normal pillow are disclosed herein. To eliminate sheer a solution using stretchable materials that do not allow the build-up of "parallel" pressures. As the skin contacts the stretchable material the pressures that would normally be created and maintained are released due to the material stretching. Therefore, as skinfolds are developing the energy is dissipated and the skin lies flat.

Essentially, as the skin moves the fabric arrangement (or at least the top layer) stretches and moves with the skin to eliminate sleep lines. The forces on a person's skin from a standard pillow increase rapidly, beyond the limit for the skin to crease. The fabric arrangement disclosed herein stretches and keeps the stress low and below the level required to create skin creasing.

Elastic Layer, Sheer Stress and Direct Pressure

A second feature of the stretchable material is that as the direct pressure of the head is applied to the pillow a constant positive sheer force is created that works to keep the skin tight. The more direct (perpendicular) force there is, the greater the positive shear becomes to keep your skin tight and free or wrinkles and creases.

Slip Layer

Although the stretchable materials would be adequate, it was found during materials testing that a second "Slip Layer" provided even greater benefit. Disclosed herein is a second layer with a slippery surface allowing the stretchable material to slide significantly improving the function of the elastic or stretchable top layer function.

Bunching Effect

A third feature of the design disclosed herein is that it overcomes material "bunching" associated with normal pillows. Bunching is reduced or eliminated as the stretchable material is always taut on the pillow. A user's head then always rests on a pillow without material waves or wrinkles. In a standard pillow the weight of a person's head can be exposed to this "bunching" of materials for hours. With the fabric arrangement formed as a pillow case, a person's head always rest on a smooth soft surface.

The present invention relates to a pillow designed to prevent skin lines and wrinkle formation while improving sleep using combinations of fabrics, cooling technologies and scents. The present invention is designed with a specific fabric and materials combination that create a surface in which the shear stresses causing skin lines and wrinkles are eliminated. Beneath the anti-wrinkle fabric combination is a layer of foam, fabric, or any other material to create a support layer for the material which also has anti-microbial properties. A third or fourth layer is composed of a cooling agent to keep the skin cool preventing damage and the phenomena of puffy eyes and swelling. The present invention includes a scent holder which allows various scents to be placed for aroma therapy while sleeping. This design overcomes the limitations of the prior inventors by specific material combinations and scents that will improve sleep, prevent wrinkles and skin lines, decreases eye swelling and facial bloating while allowing the user to sleep with a standard, normal feeling pillow.

In example embodiment, a fabric arrangement is provided that comprises at least a first panel and a second panel forming an interior space configured to accept a pillow such that the first panel and the second panel are configured to form a pillow case. Also part of this embodiment is that the first panel or the second panel comprise from the outer most layer inward a first layer comprising an elastic fabric and a second layer having a first side and a second side, the first side adjacent the first layer and comprising a low friction surface and the first layer and second layer joined at the edges and comprising the same general size. A third layer is provided and comprises a support layer configured to support the first layer and the second layer.

In one embodiment the fabric arrangement further comprises a fourth layer, the forth layer comprising a cooling material configured to absorb heat from the first layer, second layer and the third layer. In one configuration the cooling material comprises one or more of the following materials from the group of material consisting of: sodium phosphate salt, sodium ammonium phosphate salt or ammonium phosphate salt. In on embodiment the fabric arrangement further comprises a fourth layer, the forth layer comprising an anti-microbial element configured to inhibit growth of bacteria and microbes. A scent pocket configured to hold a scent infused element may also be part of this fabric arrangement. The third layer may comprise an antimicrobial and the elastic fabric preferred to be capable of stretching in any direction.

Also disclosed herein is a fabric arrangement for bedding configured to reduce the formation of wrinkles in a user's skin comprising a first layer having a top surface and a bottom surface the first layer comprising an elastic material configured to stretch in at least two directions and contact the user's skin with the top surface. A second layer is provided that has a top surface and a bottom surface such that the second layer top surface is configured to contact the bottom surface of the first layer and provide a low friction interface between the first layer bottom surface and the second layer top surface. In this embodiment a third layer is provided and configured to contact the second layer bottom surface such that the third layer comprises a support layer for the first layer and the second layer.

In one embodiment the interface between the first layer and the second layer establishes a lower coefficient of friction there between as compared to a coefficient of friction between the first layer and the skin of the user. The bedding is defined as items selected from the group consisting of sheets, pillows, blankets, pillow cases, and pillow covers. In one configuration the first layer is stretchable in 360 degrees of motion parallel to the second surface layer. In one embodiment the fabric arrangement further comprises a fourth layer comprising a pouch and a cooling layer such that the pouch is configured to contain the cooling layer and the cooling layer comprising a liquid or gel configured to conduct heat away from the skin of the user.

In one configuration the fabric is an anti-wrinkle panel for use in a pillow case such that the panel that is part of the pillow case comprises two layers. The first layer comprises a stretchable and low friction layer and it is configured as the outer layer to contact the skin of a user. The second layer below is below the first layer and it comprises a low friction layer such that the coefficient of friction between the first layer and the second layer is less than 0.3. Finally a support layer is presented under the first layer and the second layer. The support layer is configured to support the first layer and second layer and the support layer further comprises a heat conducting element as part of the support layer that conducts heat away from the first layer and second layer.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

FIG. 4 illustrates an optional inner fabric pouch configured to hold a scent element.

FIG. 5 illustrates the cooling material layer packaged either in a single container or with multiple small pockets.

DESCRIPTION OF THE INVENTION

In general, the design proposed herein employs several layers of materials, referred to herein as a fabric arrangement, configured such that when contacting the skin of the user will reduce or prevent the formation of wrinkles in the skin of the user. This fabric arrangement may be applied to or made to cover any item that touches the skin. Most often, the fabric arrangement may be configured as a pillow or pillow cover, but as described below, the fabric arrangement may be used in other environments. In other embodiment, additional elements may be combined with the fabric arrangement to provide additional benefits.

Figure 1:
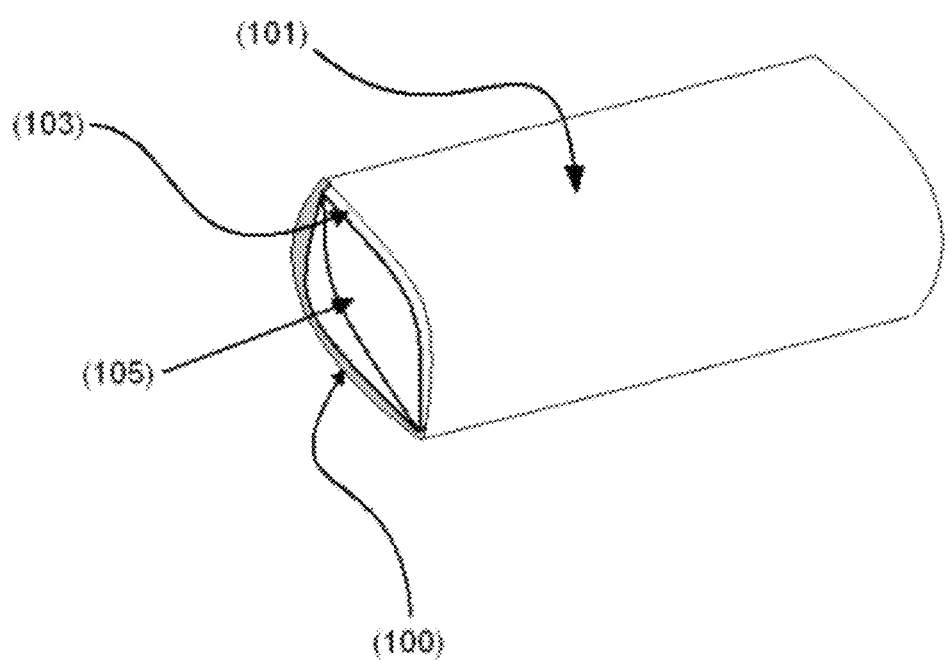
FIG. 1 illustrates an exemplary pillow having a pillow case formed form a fabric arrangement shown and described herein.

FIG. 1 illustrates an example environment of use for the fabric arrangement as set forth herein. In this embodiment the fabric arrangement is in the form of a standard pillowcase. As shown in FIG. 1, a general pillow case comprises two separate sides with a bottom side 100 and a top side 101 of fabric which are attached on three sides permanently and have an open end 103 on the forth side 110 which accepts a pillow 105. The forth side 110 can then be either left open or can be closed using means such as buttons, zippers, snaps, or any other closure device or system. The two fabric sides 100, 101 can be made similar or can be made out of two or more materials many times composed of various textures for comfort or durability or aesthetics. The top side 101 may be different than the bottom side 100. The sides which are closed may be attached by sowing, gluing, or any other closure means.

Figure 2:
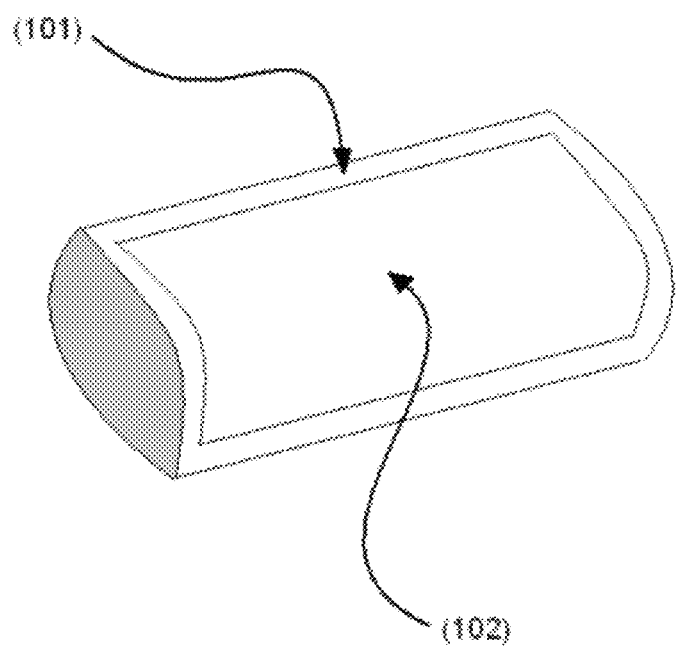
FIG. 2 illustrates the fabric arrangement as an inset or sub-portion to a pillow case top side.

In this embodiment the general configuration is that of a pillow case with standard cloth on the bottom side 100 then employs specific design on the top side 101 using several layers of fabric to create the fabric arrangement. As shown in FIG. 2, the fabric arrangement may thus be an inset 102 or sub-portion to the pillow case top side 101 for the specific area that will contact the skin of the user.

Figure 3:
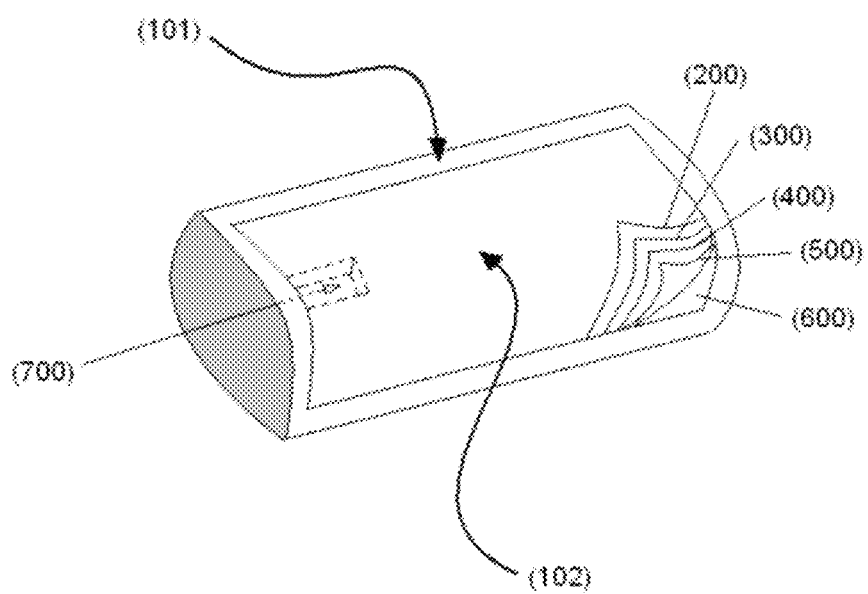
FIG. 3 illustrates one example arrangement of the fabric layers that comprises the fabric arrangement shown and disclosed herein.

Turning now to FIG. 3, one example arrangement of fabric layers is shown and disclosed. This is one example arrangement that may comprise the fabric arrangement, such as area 102 shown in FIG. 2. Generally, the layers within the specific fabric area 102 defined in order from outside to the inside are a stretchable fabric 200 on the top surface. The stretchable fabric 200 may comprise a fabric that stretches in one, two, or all dimensions. In one embodiment the material is a 360 degree stretchable fabric. The stretchable fabric may comprise but are not limited to spandex, knit fabric with elastic yarns, nylon, fabric blends, any combination of these materials, or any other material capable of stretching in more than one direction.

One preferred material for the stretchable fabric is spandex or a fabric containing spandex fibers in the fabric. Spandex is beneficial for a number of reasons. First, it can be stretched repeatedly, and will return almost exactly back to original size and shape. Second, spandex is lightweight, soft, and smooth. Additionally, spandex is easily dyed. They are also resilient since it is resistant to abrasion and the deleterious effects of body oils, perspiration, and detergents. Spandex is compatible with other materials, and can be spun with other types of fibers to produce unique fabrics, which have characteristics of both fibers. Spandex is an elastomer, thereby allowing it to be stretched to a certain degree in all directions and it recoils to its original shape when released. These fibers are superior to rubber because they are stronger, lighter, and more versatile. In some configurations, spandex fibers can be stretched to almost 500% of their length.

Spandex is sold by numerous companies under numerous different brand names including Lycra (made by Invista, previously a part of DuPont), Elaspan (also Invista's), Creora (Hyosung), ROICA and Dorlastan (Asahi Kasei), Linel (Fillattice), and ESPA (Toyobo).

Spandex is lightweight and does not restrict movement and is already used in used in athletic wear, thereby providing a comfort level among users. The form-fitting properties of spandex make it a good selection for the stretchable layer of the fabric arrangement described herein.

In the case of Style 480 spandex available from Cooper Fabrics, the machine direction M is the same as the direction of the greatest stretch of the fabric. In particular, the coefficient of friction of the Style 480 spandex at two-ply intersections or an equivalent intersection has been found to be static, dry, and about 0.25 or lower. Spandex has excellent elasticity, with the ability to stretch 270 percent or greater in the M direction and 90 percent or greater in the direction orthogonal to the M direction.

It is also contemplated that a knit fabric having knit-in elastic yarns and substantially balanced stretch characteristics may be used as the stretchable fabric. The knit may be made in the in the walewise and coursewise directions as is understood in the art of making such a fabric. The fabric can be tricot knit to include knit in elastic yarns, and forms an oscillating cable pattern in the walewise direction. Such a fabric would have good stretch characteristics in both the coursewise and walewise directions, with the stretch in the walewise direction being substantially the same as that in the coursewise direction.

In one embodiment, the stretchable fabric 200 is any material that when minimal force is applied in any direction the length changes and when the force is released the material regains its original shape. This is commonly seen in synthetic fabrics however many types to materials can be used for this purpose. The ability of the materials to stretch in any direction allows it to release any type of sheer stress that would be imparted on it. This feature therefore will not allow the human skin to build up shear stress and thus wrinkles cannot form. With facial motion during sleep, stress which normally would be imparted on the skin creating wrinkle and skin lines will not be created and the skin can relax to its normal smooth and flat configuration.

Below the stretchable fabric 200 is a generally smooth low friction material or low friction fabric layer. The low friction material 300 has at least a top surface with is low friction relative to the stretchable fabric 200 thereby allowing the stretchable fabric 200 to easily slide on top of the low friction material or not bind against the low friction material. Hence, the low friction material 300 provides a surface in which sheer forces cannot form because the two layers slide smoothly over each other allowing the stretchable fabric 200 to perform maximally. The low friction material 300 may comprise but are not limited to a medium to high thread count polyester material, a polyester, a polyester crepe back satin, a silk, a nylon, a Teflon a rayon or any other low friction material.

In one embodiment the coefficient of friction between the elastic layer and the low friction layer is between 0.5 and 0.3. In another embodiment the coefficient of friction between the elastic layer and the low friction layer is between 0.3 and 0.2. In embodiment the coefficient of friction between the elastic layer and the low friction layer is 0.25 or lower. In one embodiment the coefficient of friction between the elastic layer and the low friction layer is 0.15 or less. In one configuration the first layer and the second layer are different materials. In embodiment the outer surface of the top layer comprises cotton with a thread count of over 300 threads per inch.

In one configuration the stretchable fabric 200 is the same size or dimension as the low friction material layer 300. Movement between the stretchable fabric 200 and the low friction material layer 300 is a result of the stretchable nature of the stretchable fabric and the low friction layer below the stretchable fabric. Having the two layers the same provides a benefit of inhibiting or preventing the top layer from bunching up or overlapping when in use, which would indent, crease and wrinkle the user's skin.

In one embodiment the layers are only attached at the edges such as by sewing with thread, glue, or heat welding. This allows the inner areas of the fabric arrangement when configured in a pillow arrangement to freely slide move with the user's skin which reduces indents, creases, and wrinkles in the skin. This provides a benefit over prior are that attaches the layer near the center or where the skin contacts.

Also disclosed herein is a configuration such that both the stretchable fabric 200 and the low friction material layer 300 are both low friction materials either on one side or both sides. As can be appreciated when both layers are low friction in nature, it is less likely that the skin will bind, wrinkle and crease on the top layer this arrangement further increases smooth sliding of the top layer over the second layer. Prior designs made of cotton suffer from the drawback of not stretching and do not easily slide across one another. In addition, two slip layers provide additional slippage which reduces wrinkles.

Some prior art approaches promote having the upper layer materials as being very tight to prevent creasing and bunching, but these prior art references fail to appreciate or consider the sheer stresses on the skin as the person moves. Other prior art system only consider low friction materials which do not allow adequate shear stress dissipation. These sheer stresses can cause wrinkles. A shear stress is defined as the component of stress coplanar with a material cross section. Shear stress arises from the force vector component parallel to the cross section. Normal stress, on the other hand, arises from the force vector component perpendicular or antiparallel to the material cross section on which it acts. The design disclosed herein appreciates the interaction of the two materials (top two layers which slide relative to each other) which do not allow shear stresses to develop between the skin and the fabric while preventing bunching of those materials.

Below the low friction fabric is a support layer 400. The support layer 400 may be optional and may comprise foam, fabric, or any other material configured to support the low friction layer and provide a degree of support properties. In one embodiment the support layer 400 comprises an antimicrobial. In one embodiment the support layer 400 comprises an anti-allergen. In one embodiment the support layer comprise both a anti-allergen and a antimicrobial In one configuration the support layer 400 is designed with closed cell, thin antimicrobial foam or anti-allergen material to provide a backing for layers 200 and 300. By its added density the foam 400 further improves the function of the stretchable fabric 200 acting as a backing force. This support layer 400 also employs antimicrobial properties enhancing the property of skin protection and long term wrinkle prevention. A third function of the support layer 400 is to provide a layer of material between the user and the cooling material 600 in the event the cooling material make noise when moved, or is hard or irregular when in the pillow.

The support layer 400 may be removable to allow replacement with additional or to refresh support layer 400. The support layer 400 may be optional. The support layer 400 may comprise but are not limited to foam, fabric and thin polymer or other synthetic materials.

Below the support layer 400 is a pouch 500 formed of a thin material configured to form the pouch. The pouch 500 is sized to contain or hold a cooling material 600. The pouch 500 may be formed from any type material as would be under stood by one of ordinary skill in the art. The cooling material is configured as a layer of material or fabric configured to serve as a heat sink to conduct heat away from the skin of the user to thereby reduce heat buildup that occurs when a user's skin contacts a standard pillow for an extended period of time. As can be appreciated, heat buildup in the skin and tissue may lead to sweating, swelling, or other undesirable effects that may puff or wrinkle the skin. The cooling layer conducts heat away from the user's skin. The cooling layer and the support layer may be combined into a single layer.

The cooling layers 600 which could also be a conducting layer that provides a layer of material to reduce or eliminate that heat buildup and the associated unwanted affects. The cooling material 600 may be composed of an endothermic cooling material, water in either liquid or ice form, or other cooling gels or agents. As shown in FIG. 5, the cooling material may be packaged either in a single container 601 or with multiple small pockets 602. The cooling material may be permanently sealed or re-fillable with material. In one embodiment the cooling material is be removable and reusable. In one embodiment the material is removable and may be placed in a refrigerator or freezer to further reduces it cooling properties. In one embodiment the cooling material is heat conducting material with good thermal conductive properties to thereby sink heat away from the users skin.

In one embodiment the cooling material 600 comprises a temperature regulating membrane called Outlast made by or available from Gateway Technologies that can be inserted between any of the layers of the fabric arrangement. Alternatively, a cooling material 600 available from Frisby Technologies can be embedded in the foam layer. The foam may comprise open cell flexible polyester hydrophilic foam. In one configuration the hydrophilic foam is AQUAZONE or VPF brand material, but may also or alternatively be a Frisby product called COMFORTEMP, or the like.

It is also contemplated that the cooling material may comprise a membrane or coating can be placed on one or more sides of the foam and/or on the top layer or any other layer to conduct heat away from the user's skin. It is contemplated that if phase change technology from Outlast, Frisby, Freudenberg, Schoeller or Invista, or the like us used, it may be combined with any foam, nonwoven or insulative layer and can be on either or both sides of any layer.

It is also contemplated that the cooling material may be fibers and fabrics with reversible enhanced thermal properties, respectively which may be available from Triangle Research & Development Corp., Gateway Technologies, or Frisby. Incorporated by reference in their entirety are U.S. Pat. Nos. 4,756,958 and 5,366,801 which are directed to fibers and fabrics with reversible enhanced thermal properties. Other patents assigned to Triangle Research & Development Corp., that are related by cooling material fiber and fabric include U.S. Pat. Nos. 541,522; 5,290,904; and 5,244,356 which are also incorporated herein by reference in there entirety.

In addition, U.S. Pat. No. 5,499,460, is directed to a moldable foam insole with reversible enhanced thermal storage properties and this material can serve as the cooling material.

The disclosure of this patent is hereby incorporated by reference, and is illustrative of one type of moldable foam that can be used as mentioned herein.

Also part of this embodiment is an optional inner most fabric is formed into an additional small pouch 700 for the scent element 800 placement. The scent pocket 700 is created within the inner portion of the pillow. A scent element is created by imbedded or applied solutions with scents placed prior to inserting into the pillow. The scent element 800 is then inserted into the created small pouch 700. In various embodiments the scent element may comprise scented paper, herbs, salts, foams, fabric, cotton or encapsulated beads or pellets.

When formed as a pillow case, a standard pillow 105 is then inserted and the unit is ready for use. In other embodiment, the pillow may be sealed inside the fabric arrangement.

In an alternative embodiment the fabric arrangement is provided in other arrangements besides a pillow case. As mentioned above the fabric arrangement may be built into a pillow itself such that the pillow is self-contained within the fabric arrangement. In addition, the entire pillow case or pillow may be made of or surrounded by the fabric arrangement. In another embodiment the fabric arrangement is configured as part of a sheet set, blanket, or a bottom sheet for beddings. The fabric arrangement could also be built into clothing, such as underwear, bras, gloves, undershirts, or socks to reduce wrinkles. The fabric arrangement could also be part of furniture or a furniture cover. It is contemplated that the fabric arrangement may be configured into any article which touches skin for an extended period of time.

It is contemplated, although not required that the pillow case made from the fabric arrangement or made from a portion of the fabric is configured as generally the same size as the pillow which is placed inside the pillow case. This provides a benefit over pillow cases which are smaller than the pillow. Pillow cases which are smaller than the pillow distort the shape of the pillow and require the user to forcefully stuff the pillow into the reduced size pillow case. This prior art arrangement also makes the pillow more firm since it is compressed into a small pillow case. This changes the entire dynamic of the pillow which can cause stiffness in the neck or un-restful sleep. In addition, when the stretchable layer is in its neutral position when the user places their head on the pillow, this is less wrinkle causing than if the stretchable layer is already stretched by the compressed pillow because the stretchable layer has more capability to stretch or move with the skin than if it were pre-stretched fabric, which is in essence, not stretchable any further. The pre-stretching by the compressed pillow case takes all the stretch ability from the fabric.

In operation, the user would present the cooling layer into the pouch and then provide a pillow into the pillow case that is configured with the fabric arrangement describe herein. A user would then lay their face or head on the fabric arrangement as part of the pillow case and sleep in the normal manner. During sleep, as the user moves, the user's skin may attempt to crease or wrinkle as it moves in relation to the pillow.

With prior art pillows the pillow itself would wrinkle as the user's skin compressed the pillow or moved against the pillow. When the pillow wrinkled and creased, the user skin would likewise form into a wrinkle and could be maintained in this position for the entire evening. This also stretches the skin which leads to a loss of skin elasticity.

Using a pillow having the fabric arrangement described herein, as the user's skin moves, the top layer stretches with the moving skin, thereby preventing a crease or wrinkle from forming in either the top layer of the fabric or the user's skin. The low friction layer beneath the stretchable layer allows the stretchable layer to easily expand and contract with the movement of user by eliminating or reducing friction. As the user continues to move, the stretchable fabric moves and contracts with the user movements and skin to maintain the user's skin in smooth configuration.

The cooling element reduces heat buildup that may occur between the skin and the pillow which further reduces sweating, swelling, and puffiness.

It is contemplated that in various embodiments the various layers described herein may be arranged in any order and in various embodiment different layers may be omitted and in embodiments having omitted layers, the included layers may be arranged in any order. In one embodiment the second layer does not stretch.

While various embodiments of the invention have been described, it will be apparent to those of ordinary skill in the art that many more embodiments and implementations are possible that are within the scope of this invention. In addition, the various features, elements, and embodiments described herein may be claimed or combined in any combination or arrangement.

The invention claimed is:

1. A fabric arrangement comprising:
   at least a first panel and a second panel forming an interior space configured to accept a pillow the at least the first panel and at least the second panel configured to form a pillow case;
   at least one of the first panel or the second panel comprising from outer most layer inward:
   a first layer comprising an elastic fabric;
   a second layer having a first side and a second side, the first side adjacent the first layer and comprising a low friction surface and the first layer and second layer joined at the edges and comprising the same general size;
   a third layer comprising a support layer configured to support the first layer and the second layer; and
   a fourth layer comprising a cooling material configured to absorb heat from the first layer, second layer, and third layer.

2. The fabric arrangement of claim 1 wherein the cooling material comprises one or more of the following materials from the group of materials consisting of: sodium sulfate salt, sodium phosphate salt, sodium ammonium phosphate salt or ammonium phosphate salt.

3. The fabric arrangement of claim 1 further comprising a fourth layer, the fourth layer comprising a support layer or an antimicrobial element layer.

4. The fabric arrangement of claim 1 further comprising a scent pocket configured to hold a scent infused element.

5. The fabric arrangement of claim 1 wherein the third layer further comprises antimicrobial.

6. The fabric arrangement of claim 1 wherein the third layer comprises foam.

7. The fabric arrangement of claim 1 wherein the elastic fabric is capable of stretching in any direction.

8. A fabric arrangement for bedding configured to reduce the formation of wrinkles in a user's skin comprising:
   a first layer having a top surface and a bottom surface the first layer comprising an elastic material configured to stretch in at least two directions and contact the user's skin with the top surface;
   a second layer having a top surface and a bottom surface, the second layer top surface configured to contact the bottom surface of the first layer and provide a low friction interface between the first layer bottom surface and the second layer top surface;

a third layer configured to contact the second layer bottom surface, the third layer comprising foam and serving as a support layer for the first layer and the second layer; and a fourth layer comprising a pouch and a cooling layer, the pouch configured to contain the cooling layer and the cooling layer comprising a liquid or gel configured to conduct heat away from the skin of the user.

9. The fabric arrangement of claim 8 wherein the interface between the first layer and the second layer establishes a lower coefficient of friction there between than a coefficient of friction between the first layer and the skin of the user.

10. The fabric arrangement of claim 8 wherein bedding comprises an item selected from the group consisting of sheets, pillows, blankets, pillow cases, and pillow covers.

11. The fabric arrangement of claim 8 wherein the first layer is stretchable in 360 degrees of motion parallel to the second surface layer.

12. An anti-wrinkle panel for use in a pillow case, the panel comprising:

a first layer comprising stretchable and low friction layer, the first layer configured to contact skin of a user;

a second layer below the first layer comprising a low friction layer, wherein the coefficient of friction between the first layer and the second layer is less than 0.3; and a support layer under the first layer and the second layer, the support layer configured to support the first layer and second layer and the support layer further comprising a heat conducting element as part of the support layer that conducts heat away from the first layer and second layer.

13. The panel of claim 12, wherein the second layer is non-elastic.

14. The panel of claim 13, wherein the first layer is breathable cotton in combination with an elastic material.

15. The panel of claim 14, wherein the first layer is configured to not slip relative to the skin of a user but instead stretch with the skin of the user and the first layer slides across the second layer.

\* \* \* \* \*